(12) United States Patent
Hajianpour

(10) Patent No.: US 6,932,086 B1
(45) Date of Patent: Aug. 23, 2005

(54) SUPPORT FIXTURE FOR SETTING A FRACTURED DISTAL RADIUS

(76) Inventor: Mohammed Ali Hajianpour, 1706 Vestal Dr., Coral Springs, FL (US) 33071

(*) Notice: Subject to any disclaimer, the term of this patent is extended or adjusted under 35 U.S.C. 154(b) by 241 days.

(21) Appl. No.: 10/331,354

(22) Filed: Dec. 30, 2002

(51) Int. Cl.⁷ ............................................ A61G 15/00
(52) U.S. Cl. ...................... 128/845; 128/878; 128/879; 602/20
(58) Field of Search ................. 128/845, 846, 128/878–879; 602/20–21; 248/118.1, 118.3, 248/118.5; 606/79–88

(56) References Cited

U.S. PATENT DOCUMENTS

| | | | |
|---|---|---|---|
| 4,247,090 A * | 1/1981 | Hahn et al. ............... | 269/41 |
| 4,554,915 A | 11/1985 | Brumfield | |
| 4,747,400 A | 5/1988 | Koeneman et al. | |
| 5,006,120 A | 4/1991 | Carter | |
| 5,074,291 A | 12/1991 | Carter | |
| 5,545,162 A | 8/1996 | Huebner | |
| 5,741,251 A | 4/1998 | Benoist | |
| 6,123,704 A | 9/2000 | Hajianpour | |
| 6,197,027 B1 | 3/2001 | Hajianpour | |
| 6,318,941 B1 * | 11/2001 | Guenther ................... | 411/342 |
| 6,471,164 B2 * | 10/2002 | DiOrio ....................... | 248/118 |
| 6,626,408 B1 * | 9/2003 | Lorbiecki et al. ......... | 248/279.1 |

OTHER PUBLICATIONS

Henry Gray, F.R.S. Anatomy, Descriptive and Surgical, Facsimile of the 1901 Edition, reproduced by Barnes & Noble Books, 1995, p. 389.

* cited by examiner

Primary Examiner—Michael A. Brown
(74) Attorney, Agent, or Firm—Ronald V. Davidge

(57) ABSTRACT

A support fixture for setting a fractured distal radius includes a pair of lower support plates extending in opposite directions and a central support bracket movable away from the support plates. The support plates are pivotable relative to one another. To set a fractured distal radius, the forearm of the patient is attached to one of the support plates and his hand is attached to the other of the support plates. Then, the support plates are pivoted and clamped to achieve a desired positioning of bones adjacent to the fracture. Next, the central support bracket is moved away from the support plates, moving the patient's wrist until another desired positioning of these bones is achieved.

8 Claims, 2 Drawing Sheets

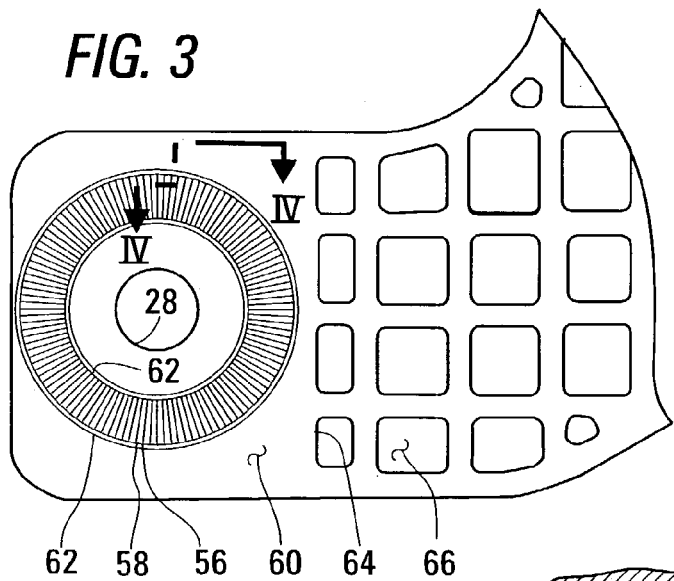
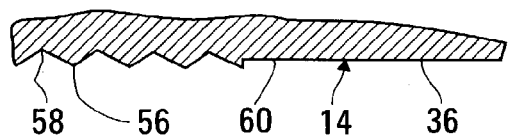
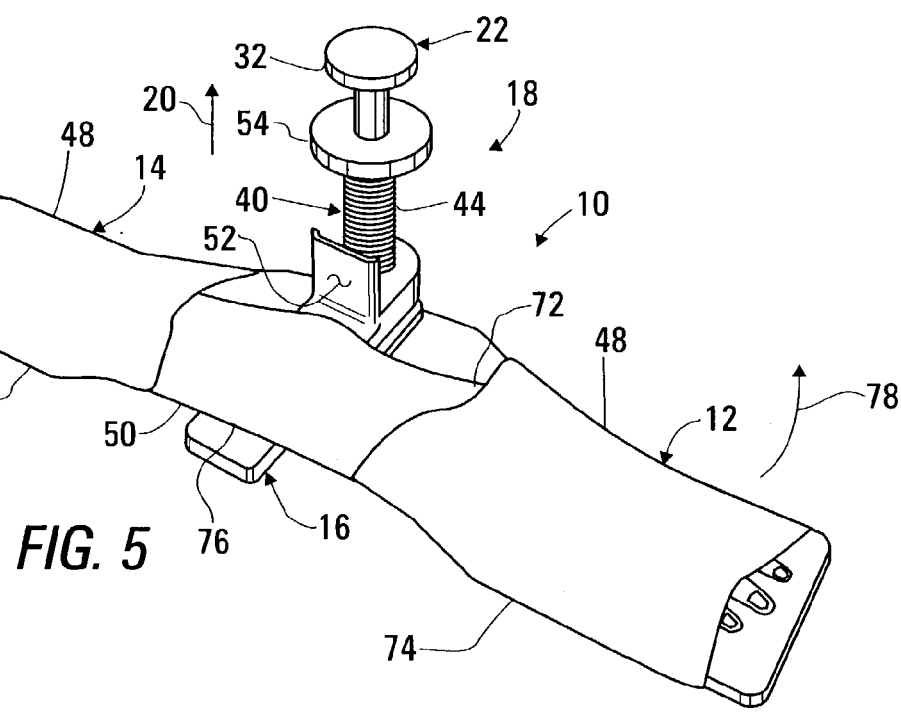

SUPPORT FIXTURE FOR SETTING A FRACTURED DISTAL RADIUS

BACKGROUND OF THE INVENTION

1. Field of the Invention

This invention relates to an apparatus and method for use in the setting, or reduction, of a fractured distal radius.

2. Background Information

The fracture of the distal radius is one of the most common human fractures, occurring in as many as 350,000 people per year in the United States alone. The application of an extension force and lateral depression for reducing a fracture of the distal radius is well known, having been described in the 1901 edition of Gray's Anatomy in the following manner, "The treatment consists in flexing the forearm, and making a powerful extension from the wrist and elbow, depressing at the same time the radial side of the hand, and retaining the parts in that position by well-padded pistol-shaped splints."

Conventional methods for reducing a fractured distal radius require that the physician or surgeon must be helped by an assistant during the process. Two or more people are required to apply the extension force to the hand into a configuration providing an additional extension force at the site of the fracture, and to further manipulate any bone fragments or separated sections into position. What is needed is a convenient fixture for applying such forces during the process of setting this type of fracture, so that a physician or surgeon can reduce the fracture without requiring the help of an assistant.

U.S. Pat. No. 6,123,705 describes a support fixture for setting a fractured distal radius includes a housing having a strap for fastening the fixture to the patient's forearm, a sliding section, sliding within the housing as a screw is rotated, and a pivoting section extending from a distal end of the sliding section. The sliding section also includes a structure for supporting the patient's wrist. The distal end of the pivoting section includes a pair of fingertraps. Two of the patient's fingers are held in the fingertraps, while an extension force is applied between his forearm and hand through the rotation of the screw, and while his hand is twisted by adjusting the angle of the pivoting section to increase the gap between fractured sections of bone, causing reduction of the fracture to occur.

U.S. Pat. No. 5,074,291 describes a hand traction surgical table having an adjustable surgical table frame. An arm board having an upper surface and a lower surface is mounted on the surgical table frame, thereby providing an operating surface for surgical procedures on the wrist and forearm. A pulley is mounted on the surgical table frame, and a reduction force applying cable is mounted through the pulley. A finger retention device is mounted at a first end of a cable and a force applicator is mounted at a second end of the cable so that a predetermined reduction force can be applied to the patient's hand.

U.S. Pat. No. 5,006,120 shows the use of a device including a weight, a pulley, and fingertraps to hold a patient's arm extended, reducing a distal fracture of the radius during an operation installing, with a number of screws and blades extending into the bone, a plate spanning a fracture of the distal radius. What is needed, is a convenient means to support the wrist, from below and from a side, in a manner that the angle of the wrist can be controlled during the setting of such a fracture, and, for example, during the installation of a plate spanning a fracture of the distal radius.

A number of other patents, such as U.S. Pat. Nos. 4,554,915, 5,545,162, 5,741,251, and 6,197,027 describe external fixation frames which are used, for example, for immobilizing bone segments adjacent a fracture or joint. Again, what is needed is a convenient means to support the wrist in a manner that the angle of the wrist can be controlled during the installation of an external fixation frame.

SUMMARY OF THE INVENTION

According to a first aspect of the invention, there is provided a support fixture for setting a fractured distal radius of a forearm. The support fixture includes a central mounting structure, a pair of support brackets a clamping member, and a central support bracket. The pair of support plates extends along a first plane in opposite directions from the central mounting structure and pivotable on the central mounting structure in the first plane relative to one another. The clamping member is engageable to hold the support plates in a fixed relationship with one another. The central support bracket extends from the central mounting structure spaced apart from the support plates and is movable perpendicular to the first plane along the central mounting structure.

BRIEF DESCRIPTION OF THE FIGURES

FIG. 3 is a bottom plan view of a support plate within the support fixture of FIG. 1;

FIG. 4 is a vertical cross-sectional elevation of the support plate of FIG. 3, taken as indicated by section lines IV—IV therein; and FIG. 5 is a perspective view of the support fixture of FIG. 1 in use to set a fracture of a distal radius.

DETAILED DESCRIPTION OF THE INVENTION

Figure 1:
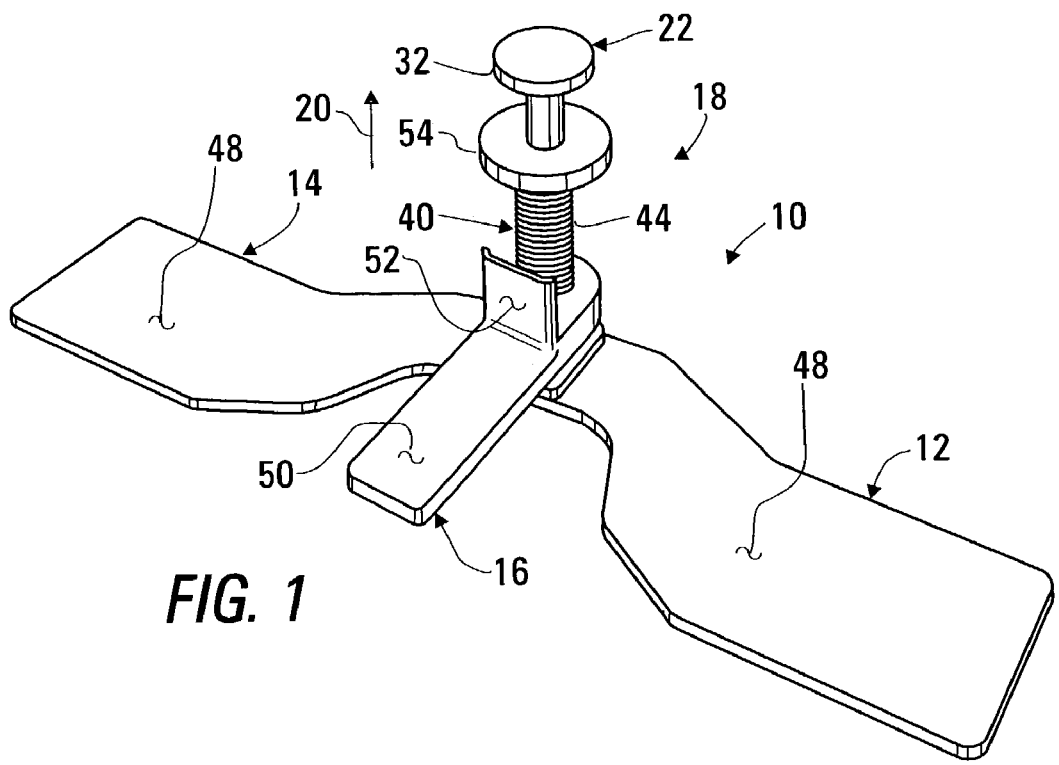
FIG. 1 is a perspective view of a support fixture built in accordance with the present invention.

FIG. 1 is a perspective view of a support fixture 10 built in accordance with the present invention. The support fixture 10 includes a first support plate 12, a second support plate 14, a central support bracket 16, and a central mounting structure 18 mounting the support plates 12, 14 to pivot relative to one another and further mounting the central support bracket 16 to move in or opposite the direction of arrow 20, perpendicular to a plane in which the support plates 12, 14 extend.

Figure 2:
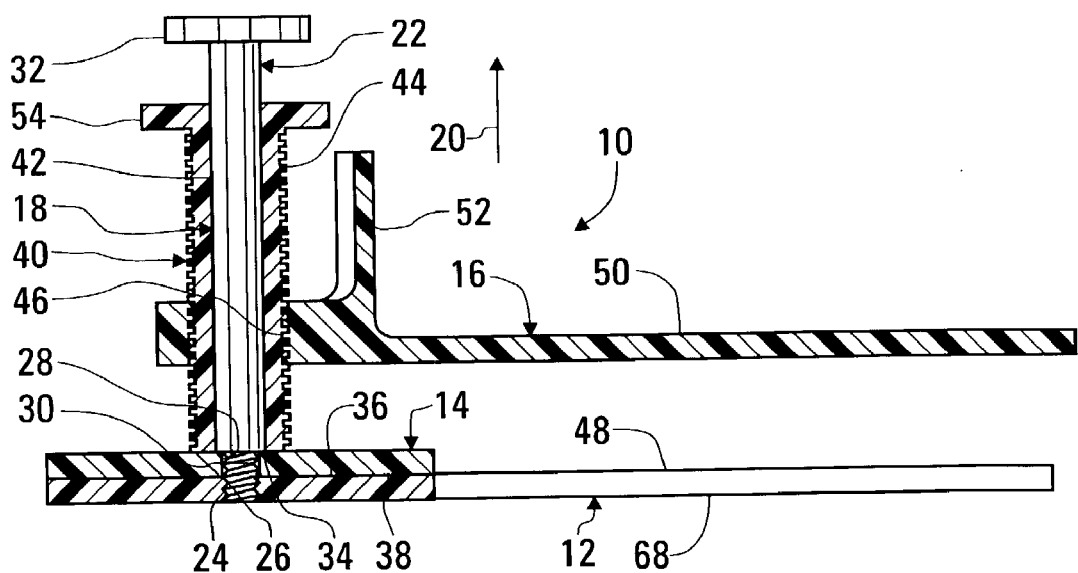
FIG. 2 is a vertical cross-sectional elevation of the support fixture of FIG. 1, taken through a central mounting structure therein.

FIG. 2 is vertical cross-sectional elevation of the support fixture 10, taken through the central mounting structure 18 to show the arrangement thereof. The central mounting structure 18 includes a clamping member 22 having a threaded surface 24 engaging a threaded hole 26 within the first support plate 12. The clamping member 22 additionally includes a bearing surface 28, axially aligned with the threaded surface 24 to extend through a clearance hole 30 in the second support plate 14, and a knob 32 used to rotate the clamping member 22. When the threaded surface 24 is loosely held (i.e., not tightened) within the threaded hole 26 of the first support plate 12, the second support 12 pivots on the bearing surface 28, relative to the first support plate 12 within the plane in which the support plates 12, 14 extend. Threads from the threaded hole 26 may extend around some or all of the bearing surface 28. When the threaded surface 24 is tightened within the threaded hole 26, a shoulder 34 of the clamping member 22 holds the lower surface 36 of the upper support plate 14 against the adjacent upper surface 38 of the support plate 12, preventing rotation of these plates 12, 14 relative to each other.

The central mounting structure 18 also includes a bracket screw member 40, rotatably mounted on pivot shaft portion 42 of the clamping member 22. The bracket screw member 40 includes an externally threaded surfaces 44 engaging a threaded hole 46 within the central support bracket 16, so that rotation of the bracket screw member 40 relative to the central support bracket 16 moves the central support bracket 16, relative to the bracket screw member 40, in or opposite the direction of arrow 20, perpendicular to the plane in which the support plates 12, 14 extend.

Each of the support plates 12, 14 has an upper surface 48 for supporting either the hand or forearm of the patient. The central support bracket 16 has a support surface 50 for supporting the wrist of the patient as it is elevated above the lower surfaces of the hand and forearm and a wall 52 extending outward from the support surface 50 to restrain rotation of the central support bracket 16 as bracket screw member 40 is rotated by means of a knob 54 to move the central support bracket 16 in or opposite the direction of arrow 20.

FIG. 3 is a fragmentary bottom plan view of the second support plate 14, showing a pattern of radially-extending ridges 56 and grooves 58 on the lower surface 36 of this plate 14 around the clearance hole 28.

FIG. 4 is a fragmentary vertical cross-sectional view of the second support plate 14, taken as indicated by section lines IV—IV in FIG. 3, showing adjacent ridges 56 and grooves 58.

Referring to FIGS. 2–4, the lower surface 36 of the second support plate 14 and the upper surface 38 of the first support plate 12 each include similar, mating patterns of ridges 56 and grooves 58, which extend below and above the adjacent flat area 60 of the lower surface 36. When these surfaces 36 and 38 are held together by tightening the threaded surface 24 of the clamping member 22 within the threaded hole 26 of the first support plate 12, the ridges 56 and grooves 58 form matching serrations that prevent pivoting movement of the support plates 12, 14 relative to one another. That is, the engagement of ridges 56 of the second support plate 14 within grooves 58 of the first support plate 12, together with the engagement of ridges 56 of the first support plate 12 within grooves 58 of the second support plate 14. On the other hand, when the surfaces 36 and 38 are allowed to move apart by loosening the threaded surface 24 of the clamping member 22 within the threaded hole 26 of first support plate 12, the ridges 56 of the first support plate 12 can move past the ridges 56 of the second support plate 14, so that the support plates 12, 14 may be pivoted relative to one another. The surfaces 36, 38 additionally include recessed annular grooves 62 to accommodate misalignment between the patterns of ridges 56 and grooves 58 on the first and second support plates 12, 14.

The lower surface 36 of the second support plate 14 preferably includes a waffle pattern of cavities 64 extending upward to webs 66 extending along the upper surface 48 of this plate 14. Preferably, the lower surface 68 of the first support plate 12 additionally includes a similar pattern of cavities 60. These cavities 60, reduce the amount of plastic resin needed to produce parts having sufficient stiffness and simplify the process of molding parts with suitable stiffness.

The process for setting, or reducing a fractured distal radius in accordance with the present invention will now be discussed in reference to FIG. 5, which is a perspective view of the support fixture 10 as used to perform this process with the forearm 70 and hand 72 of the patient each being fastened to the support plates 12, 14 of the support fixture 1 by means of a web 74, and with the wrist 76 disposed adjacent to the central support bracket 18. For example, each of the webs 74 may be a strip of self-adherent bandage sold under the registered trademark MEDI-RIP by Hartmann-Conco of Rock Hill, S.C. Such a material clings to itself when wrapped tightly more than once around the forearm 70 or hand 72. Alternately, the webs 74 may each be formed as part of the apparatus 10, with two parts of a textile web being joined by loop and hook closure pads sold under the registered trademark VELCRO. The forearm 70 and hand 72 are oriented on the apparatus 10 so that the central mounting structure 18 is disposed laterally outward from the forearm 70, with the hand being attached to either the first support structure 12, as shown in FIG. 5, or the second support structure 14, to place the central mounting structure 18 outside the forearm 70, regardless of whether the right or left forearm is being treated.

After the forearm 70 and hand 72 are fastened to the apparatus 10 by means of the webs 74, a process of manipulation of the apparatus 10 to set the fracture is begun, preferably to be carried out with the aid of fluoroscopic visualization of the fracture area to determine when a desirable relationship among the fractured bone structures has been attained. The various elements of the apparatus 10 are preferably composed of materials, such as thermoplastic resins, that are transparent to the radiation used for fluoroscopic visualization.

This process of manipulation of the apparatus 10 begins with manually adjusting the angular relationship the first and second support plates with the clamping member loosened to permit relative pivoting movement of these plates. First, the support plates 12, 14 are manually pivoted relative to one another so that the hand 72 is pivoted laterally outward, in the direction of arrow 78. When the desired relationship of the bones in the fracture area has been attained in this way, preferably as verified by fluoroscopic visualization, the support plates 12, 14 are locked together by tightening the clamping member 22 by rotating the knob 32. Then, the central support bracket 16 is moved away from the lower support plates 12, 14 by rotating the knob 54 to turn the bracket screw member 40. When the central support 16 has moved the wrist 76 so that the bones adjacent the fracture are moved into a desirable position, again preferably as verified through fluoroscopic visualization, this manipulation process is determined to have been completed.

At this point, the position of bones adjacent the fracture may by further maintained by attaching an external fixation device, such as the device described in U.S. Pat. No. 6,197,027, the disclosure of which is incorporated herein by reference, so that various pins extend into these bones. Alternate fixation means, including the attachment internal of screws and plates to hold the bones together, as well known to those skilled in the art, may alternately be employed. Portions of the webs 74 may be cut away to clear surgical sites, or two or more straps may be used in place of a web, so that access to surgical sites will not be impaired.

While the invention has been described in its preferred form or embodiment with some degree of particularity, it is understood that this description has been given only by way of example and that numerous changes in the details of construction, fabrication and use, including the combination and arrangement of parts, may be made without departing from the spirit and scope of the invention.

I claim:

1. A support fixture for setting a fractured distal radius of a forearm, wherein said support fixture comprises:
   a central mounting structure;
   a pair of support plates, extending along a first plane in opposite directions from said central mounting structure and pivotable on said central mounting structure in said first plane relative to each other;
   a clamping member engageable to hold said support plates in a fixed relationship with one another; and
   a central support bracket extending from said central mounting structure spaced apart from said support plates and movable perpendicular to said first plane along said central mounting structure.

2. A support fixture for setting a fractured distal radius of a forearm, wherein said support fixture comprises:
   a central mounting structure;
   a pair of support plates, extending along a first plane in opposite directions from said central mounting structure and pivotable on said central mounting structure in said first plane relative to each other, wherein a first support plate within said pair of support plates includes a threaded hole, and wherein a second support plate within said pair of support plates includes a clearance hole;
   a clamping member engageable to hold said support plates in a fixed relationship with one another, wherein said clamping member includes a threaded surface engaging said threaded hole of said first support plate, a bearing surface extending through said clearance hole of said second support plate, axially aligned with said threaded surfaces, and a shoulder holding adjacent surfaces of said first and second support plates together as said threaded surface is tightened in engagement with said threaded hole of said first support plate; and
   a central support bracket extending from said central mounting structure spaced apart from said support plates and movable perpendicular to said first plane along said central mounting structure.

3. The support fixture of claim 2, wherein said adjacent surfaces of said first and second support plates include matching serrations engaging one another to prevent pivoting movement of said first and second support plates relative to one another as said adjacent surfaces of said first and second support plates are held together.

4. The support fixture of claim 2, wherein
   said clamping member additionally includes a pivot shaft portion,
   said central mounting structure includes a bracket screw member having an external screw thread and a hole pivotally mounting said bracket screw member on said pivot shaft portion of said clamping member, and
   said central support bracket includes a threaded hole engaging said external screw thread of said bracket screw member.

5. The support fixture of claim 4, wherein said clamping member includes a knob.

6. A support fixture for setting a fractured distal radius of a forearm, wherein said support fixture comprises:
   a central mounting structure;
   a pair of support plates, extending along a first plane in opposite directions from said central mounting structure and pivotable on said central mounting structure in said first plane relative to each other;
   a clamping member engageable to hold said support plates in a fixed relationship with one another;
   a central support bracket extending from said central mounting structure spaced apart from said support plates and movable perpendicular to said first plane along said central mounting structure; and
   a web extending around each support plates in said pair of support plates for attachment of a body member of said patient to said support plate.

7. The support fixture of claim 6, wherein said web is composed of a strip of self-adherent bandage material.

8. A support fixture for setting a fractured distal radius of a forearm, wherein said support fixture comprises:
   a central mounting structure, including a pivot shaft, a bracket screw member having an external screw thread and a hole pivotally mounting said bracket screw member on said pivot shaft of said central mounting structure;
   a pair of support plates, extending along a first plane in opposite directions from said central mounting structure and pivotable on said central mounting structure in said first plane relative to each other;
   a clamping member engageable to hold said support plates in a fixed relationship with one another; and
   a central support bracket extending from said central support structure spaced apart from said support plates and movable perpendicular to said first plane along said central support structure, wherein said central support bracket includes a threaded hole engaging said external screw thread of said bracket screw member.

* * * * *